United States Patent [19]

Dines

[11] 4,094,893
[45] June 13, 1978

[54] ISONITRILE INTERCALATION COMPLEXES

[75] Inventor: Martin B. Dines, Westfield, N.J.

[73] Assignee: Exxon Research & Engineering Co., Linden, N.J.

[21] Appl. No.: 744,637

[22] Filed: Nov. 24, 1976

[51] Int. Cl.² .......................... C07F 11/00; C07F 7/00; C07F 7/28
[52] U.S. Cl. ................. 260/429 R; 250/272; 252/25; 252/518; 252/519; 252/520; 260/429.3; 260/429.5
[58] Field of Search ............ 260/429.3, 429.5, 429 R; 250/272; 252/518, 519, 520, 25

[56] References Cited

U.S. PATENT DOCUMENTS

| | | | |
|---|---|---|---|
| 3,408,310 | 10/1968 | McConnell | 252/512 |
| 3,688,109 | 8/1972 | Gamble | 250/51.5 |
| 3,763,043 | 10/1973 | Thompson | 252/518 X |
| 3,766,064 | 10/1973 | Gamble et al. | 252/25 |
| 3,769,210 | 10/1973 | Cais et al. | 252/25 |
| 3,933,688 | 1/1976 | Dines | 252/518 R X |
| 3,957,696 | 5/1976 | Van Lier | 252/518 R |
| 3,980,684 | 9/1976 | Dines | 260/429.3 |

OTHER PUBLICATIONS

Meyer et al., The Journal of Chemical Physics, 62 4411–4419 (1975).
Ishizawa, Kotai Butsuri 8 (2), pp. 103–107 (1973).
Rao et al., Materials Research Bulletin, 9 (7), 921–926 (1974).
Crocani et al., Chemical Abstracts, 78 148047b, (1973).

Primary Examiner—Helen M. S. Sneed
Attorney, Agent, or Firm—Joseph J. Allocca

[57] ABSTRACT

A complex is described of the formula:

$$TX_2(RNC)_y$$

wherein $TX_2$ is the inorganic host in which T is selected from the group consisting of titanium, zirconium, hafnium, vanadium, niobium, tantalum, molybdenum and tungsten and mixtures thereof, and X is a chalcogenide selected from the group consisting of sulfur, selenium and tellurium, and RNC is the organic guest wherein R is an alkyl or aryl alkyl radical of from 1 to 18 carbon atoms and $y$ is a number ranging from about 0.10 to about 2.0.

These new complexes are afforded by the intercalation of organic isonitriles within the layered structure of Group IVb, Vb, molybdenum and tungsten transition metal dichalcogenides.

15 Claims, No Drawings

ISONITRILE INTERCALATION COMPLEXES

DESCRIPTION OF THE INVENTION

A complexes is described of the formula:

$$TX_2(RNC)_y$$

wherein $TX_2$ is the inorganic host in which T is selected from the group consisting of titanium, hafnium, vanadium, niobium, tantalum, molybdenum and tungsten and mixtures thereof, and X is a chalcogenide selected from the group consisting of sulfur, selenium, tellurium and mixtures thereof and RNC is the isonitrile organic guest wherein R is an alkyl or aryl alkyl radical of from 1 to 18 carbon atoms, preferably 1-7 carbon atoms and $y$ is a number ranging from about 0.10 to about 2.0. These new complexes are afforded by the intercalation of organic isonitriles within the layered structure of Group IVb, Vb, molybdenum and tungsten transition metal dichalcogenides.

Organic nitriles and isonitriles have a contrasting coordination chemistry which is representative of the full spectrum of Lewis acid-base behavior. In the nitriles, the basic character is localized on the nitrogen which possesses an unshared pair of electrons, while for the isonitriles, carbon bears the orbitals of ligation. Examination of the accepted formula representations of these material dramatically highlights this pnenomenon which results from the reversal of the atoms bonded to the organic group.

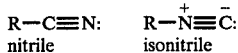

nitrile          isonitrile

The intercalation complexes of the instant invention $TX_2(RNC)_y$ ar clearly distinguishable from compounds described in U.S. Pat. NO. 3,766,064 to Gamble in that in the instant compounds, the donor atom, i.e., the atom required to intercalate, is not nitrogen but rather carbon. In Gamble, intercalates utilizing ammonia, hydrazine and organic nitrogen compounds are described in which the intercalating atom is nitrogen. Attempting to intercalate nitriles however, is furitless since nitriles do not intercalate.

Intercalate complexes have become of major interest only as a result of the failure of petroleum-based lubricants to satisfactorily perform at high sustained loading, high temperatures, extremely low temperatures, or in a vacuum. Solid lubricants, by way of comparison, are unaffected by such variations in operating environment.

The instant invention is directed to a new group of intercalated complexes of the formula:

$$TX_2(RNC)_y$$

wherein T is selected from the group consisting of titanium, zirconium, hafnium, vanadium, niobium, tantalum, molybdenum and tungsten and mixtures thereof, X is a chalcogenide selected from the group consisting of sulfur, selenium and tellurium, and RNC is an isonitrile where R is a $C_1$ to $C_{18}$ hydrocarbyl radical selected from the group consisting of $C_1$ to $C_{18}$ linear and branched alkyl, preferably $C_1$ to $C_7$, $C_3$ to $C_{18}$ cyclic alkyl, preferably $C_3$ to $C_7$, and $C_7$ to $C_{18}$ aryl alkyls, and $y$ is a number ranging from 0.10 to 2.0, preferably 0.3 to 1.0.

The complexes of the instant invention have utility as lubricants, x-ray diffraction gratings and as superconductors. The increase observed for the superconducting transition temperature in the compound $TaS_2 - (CH_3NC)_{0.75}$ was higher than any other such molecular intercalate prepared thus far. The Tc value is 5.8° K. The complex $TaS_2(BuNC)_{0.5}$ is also marked by a high superconducting transition temperature, Tc = 5.2° K.

EXPERIMENTAL

All work was carried out in a dry box or under a blanket of nitrogen. Tantalum and titanium disulfides were prepared by high temperature contact of the elements with subsequent vapor transport (a well-known procedure) and were pure as seen by their x-ray diffraction patterns. $MoS_2$ was prepared via the low temperature nonaqueous precipitation technique using $MoCl_4 + 2Li_2S$ (Ser. No. 641,424 F Dec. 17, 1975) and was of small crystal size (ca 0.1 $\mu$). Butyl and benzylisonitrile were used as obtained from the supplier, Aldrich Chemicals. Methylisonitrile was prepared according to the method outlined in "Organic Synthesis", Collective Vol. V, et. H. E. Baumgarten, pg. 772. All intercalations were run in sealed tubes using about 1 g of dichalcogenide and an excess of isonitrile, an excess being 2 moles or more isonitrile per mole dichalcogenide. Contacting was for a period of four days at the listed temperatures; however, times may range from minutes to weeks, while temperature can range from ambient to 200° C. The product was isolated, preferably by filtering, washed with methylene chloride and dried.

TABLE I
SUMMARY OF RESULTS (4 DAYS CONTACT)
$TS_2(RNC)_y$

| T  | R              | Temp(° C) | y    | Interlayer Expansion | $T_c$ (° K) |
|----|----------------|-----------|------|----------------------|-------------|
| Ta | $CH_3$—        | 100°      | 0.5  | 3.7 A                | 5.8         |
| Ti | $CH_3$—        | 150°      | 0.5  | 3.7                  | —           |
| Ta | $C_4H_9$—      | 125°      | 0.5  | 4.2                  | 5.2         |
| Mo | $C_4H_9$—      | 130°      | 0.16 | (amorphous)          | —           |
| Ta | Benzyl-($C_7H_7$—) | 150° | 0.5  | 12.0                 | —           |

Changes in the x-ray powder diffraction patterns of the host are evidence that the products formed by heating together the transition metal dichalcogenide and the isonitrile are actually intercalation products. These changes evidence a spreading apart of the composite $TX_2$ sheets by an amount corresponding to the molecular dimensions of the isonitrile guest. Thus, methylisonitrile products of both $TiS_2$ and $TaS_2$ show a dilation of about 4 A. For butylisonitrile the value of $TaS_2$ interlayer expansion is 4.2 A.

To demonstrate the difference between nitrile and isonitrile as to intercalation, the above experiment was repeated using acetonitrile. After 4 days at 125° C no detectable reaction with $TaS_2$ was observed either by weight gain or x-ray powder diffraction analysis. Under identical conditions methylisonitrile reacted to completion with $TaS_2$.

The intercalation reactions are reversible, such reversal being accomplished by heating the products to temperatures ranging from 100°–400° C. The weight loss was recorded in a differential thermal analyzer (Tga) and was found to approximately correspond to the uptake of the organic material.

To determine whether the organic material being intercalated was truly the isonitrile and not the isomerization product (nitrile), the deintercalation products recovered by the TGA for the deintercalation of $TaS_2$ (C₄H₉NC) was analyzed by infrared technique. The absorption band at 2160 cm⁻¹ showed only isonitrile.

Examples of complexes within the scope of the general formula are:

TaS₂ (CH₃NC)₀.₇₅

TaS₂ (C₄H₅NC)₀.₅
TaS₂ (C₆H₅CH₂NC)₀.₇₅
TiS₂ (CH₃NC)₀.₅
TaS₂ (C₆H₅CH₂NC)₂
TiS₂ (C₂H₅NC)₀.₃
ZrS₂(C₃H₇NC)₀.₃
NbS₂ (CH₃NC)₀.₅
VSe₂ (C₄H₉NC)₀.₅
HfSe₂ (C₂H₅NC)₀.₅
WSe₂ (CH₃NC)₀.₂₅
MoS₂ (C₄H₉NC)₀.₁₆

What is claimed is:

1. Complexes of the formula:

TX₂(RNC)_y wherein TX₂ is the inorganic host in which T is a transition metal selected from the group consisting of titanium, zicronium, hafnium, vanadium, niobium, tantalum, molybdenum and tungsten and mixtures thereof and X is a chalcogenide selected from the group consisting of sulfur, selenium and tellurium and RNC is the isonitrile organic guest wherein R is selected from the group consisting of C₁ to C₁₈ linear and branched alkyls, C₃ to C₁₈ cyclic alkyls and C₇ to C₁₈ aryl alkyls and y is a number ranging from 0.10 to 2.0.

2. The complexes of claim 1 wherein T is selected from the group consisting of titanium, zirconium, hafnium, vanadium, niobium and tantalum, and X is a chalcogenide selected from the group consisting of sulfur, selenium and tellurium.

3. The complexes of claim 1 wherein T is selected from the group consisting of titanium, tantalum, zirconium, and vanadium, and X is a chalcogenide selected from the group consisting of sulfur, selenium and tellurium.

4. The complexes of claim 1 wherein T is selected from the group consisting of titanium and tantalum, X is sulfur, R is selected from the group consisting of C₁ to C₁₈ linear and branched alkyls, and C₇ to C₁₈ aryl alkyls and y is a number ranging from 0.3 to 1.0.

5. The complexes of claim 1 wherein R is selected from the group consisting of C₁–C₇ straight or branched chain alkyl, C₃–C₇ cyclic alkyls.

6. The complex of claim 1 of the formula: TaS₂ (CH₃NC)₀.₅.

7. The complex of claim 1 of the formula: TaS₂ (C₄H₉NC)₀.₅.

8. The complex of claim 1 of the formula: TaS₂ (C₆H₅CH₂NC)₂.

9. The complex of claim 1 of the formula: TiS₂ (C₂H₅NC)₀.₃.

10. The complex of claim 1 of the formula: ZrS₂ (C₃H₇NC)₀.₃.

11. The complex of claim 1 of the formula: NbS₂ (CH₃NC)₀.₅.

12. The complex of claim 1 of the formula: VSe₂ (C₄H₉NC)₀.₅.

13. The complex of claim 1 of the formula: HfSe₂ (C₂H₅NC)₀.₅.

14. The complex of claim 1 of the formula: WSe₂ (CH₃NC)₀.₂₅.

15. The complexes of claim 4 wherein R is selected from the group consisting of C₁–C₇ straight or branched chain alkyl, C₃–C₇ cyclic alkyls.

* * * * *